United States Patent
Liu et al.

(10) Patent No.: US 8,552,243 B2
(45) Date of Patent: Oct. 8, 2013

(54) PROCESS FOR PREPARING AN ALKYLATE

(75) Inventors: Zhichang Liu, Beijing (CN); Chunming Xu, Beijing (CN); Rui Zhang, Beijing (CN); Xianghai Meng, Beijing (CN); Ana Cecilia Patroni, Amsterdam (NL); Peter Anton August Klusener, Amsterdam (NL); Albertus Vincentius Petrus Van Den Bosch, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/388,478

(22) PCT Filed: Aug. 5, 2010

(86) PCT No.: PCT/EP2010/061440
§ 371 (c)(1),
(2), (4) Date: Mar. 23, 2012

(87) PCT Pub. No.: WO2011/015636
PCT Pub. Date: Feb. 10, 2011

(65) Prior Publication Data
US 2012/0178982 A1    Jul. 12, 2012

(30) Foreign Application Priority Data

Aug. 6, 2009 (WO) ................ PCT/CN2009/000890

(51) Int. Cl.
*C07C 2/56* (2006.01)

(52) U.S. Cl.
USPC ............................ 585/719; 585/716; 585/709

(58) Field of Classification Search
None
See application file for complete search history.

(56) References Cited

U.S. PATENT DOCUMENTS

| 7,285,698 B2 | 10/2007 | Liu et al. | 585/721 |
| 2004/0133056 A1 | 7/2004 | Liu et al. | 585/721 |

FOREIGN PATENT DOCUMENTS

CN    101244972    8/2008

*Primary Examiner* — Tam M Nguyen
(74) *Attorney, Agent, or Firm* — Charles W. Stewart

(57) ABSTRACT

The present invention provides a process for preparing an alkylate, comprising: contacting in a reaction zone a hydrocarbon mixture comprising at least isoparaffin and an olefin with an acidic ionic liquid catalyst under alkylation conditions to obtain an alkylate; withdrawing an alkylate-comprising effluent from the reaction zone; separating at least part of the alkylate-comprising effluent into an hydrocarbon-rich phase and an ionic liquid catalyst-rich phase; fractionating part of the hydrocarbon-rich phase into at least an alkylate-comprising product and a isoparaffin-comprising stream; mixing another part of the hydrocarbon-rich phase with an olefin-comprising stream to form the hydrocarbon mixture; and providing the hydrocarbon mixture to the reaction zone.

15 Claims, 2 Drawing Sheets

PROCESS FOR PREPARING AN ALKYLATE

PRIORITY CLAIM

The present application claims priority from PCT/EP2010/061440, filed 5 Aug. 2010, which claims priority from PCT/CN2009/000890, filed 6 Aug. 2009.

FIELD OF THE INVENTION

The present invention provides a process for preparing an alkylate.

BACKGROUND OF THE INVENTION

There is an increasing demand for alkylate fuel blending feedstock. As a fuel-blending component alkylate combines a low vapour pressure, no sulphur, olefins or aromatics with high octane properties.

Almost all alkylate is produced by reacting isobutane with butene in the presence of a suitable acidic catalyst. The most used catalysts are HF and sulphuric acid, although other catalysts such a solid acid catalyst have been reported. Recently, the alkylation of isoparaffins with olefins using an acidic ionic liquid catalyst has attracted attention as an alternative to HF and sulphuric acid catalysed alkylation processes.

In for instance U.S. Pat. No. 7,285,698 a process for manufacturing an alkylate oil is disclosed, which uses a composite ionic liquid catalyst to react isobutane with a butene. In the process of U.S. Pat. No. 7,285,698, isobutane and butene are supplied to a reactor and the alkylate is formed by contacting the reactants with a composite ionic liquid under alkylation conditions. The reactor effluent is separated and the ionic liquid phase is recycled to the reactor while the hydrocarbon phase is treated to retrieve the alkylate. A disadvantage of the process of U.S. Pat. No. 7,285,698 is that the ratio of isobutane to butene in the feed to the process is too low when using ionic liquid catalyst. Therefore, a large hold up of isobutane in the reactor is required to provide a high isobutane to butene ratio.

In CN1012449752, a method for preparing an alkylate is disclosed wherein in a reactor isobutane is reacted with a liquid olefin in the presence of an ionic liquid catalyst to obtain an alkylate. In CN1012449752, a high isobutane to olefin ratio in the reactor is maintained by recycling part of the hydrocarbons, including isobutane, in the reactor effluent. Separately, the catalyst is recycled to the reactor. In CN1012449752, a raw mixture of isobutane and olefins having a low isobutane to olefin ratio is fed to the reactor. This raw mixture is directly provided into the reactor resulting in localised high olefin concentrations in the reactor. Such high olefin concentrations induce side reactions such as olefin polymerisation.

SUMMARY OF THE INVENTION

It has been found that the high olefin concentration in the reaction zone of an ionic liquid alkylation process may be reduced during operation of an ionic liquid alkylation process ensuring that the hydrocarbon mixture, which is provided to the relation zone, comprises isoparaffin and olefin a high isoparaffin to olefin ratio.

Accordingly, the present invention provides a process for preparing an alkylate, comprising:

contacting in a reaction zone a hydrocarbon mixture comprising at least isoparaffin and an olefin with an acidic ionic liquid catalyst under alkylation conditions to obtain an alkylate;

withdrawing an alkylate-comprising effluent from the reaction zone;

separating at least part of the alkylate-comprising effluent into an hydrocarbon-rich phase and an ionic liquid catalyst-rich phase;

fractionating part of the hydrocarbon-rich phase into at least an alkylate-comprising product and an isoparaffin-comprising stream;

mixing another part of the hydrocarbon-rich phase with an olefin-comprising stream to form the hydrocarbon mixture; and providing the hydrocarbon mixture to the reaction zone.

A high isoparaffin to olefin ratio is maintained throughout the reaction zone by mixing the olefin-comprising stream with at least part of the hydrocarbon-rich phase prior to introducing the olefin-comprising stream into the reaction zone.

DETAILED DESCRIPTION OF THE INVENTION

Figure 1:
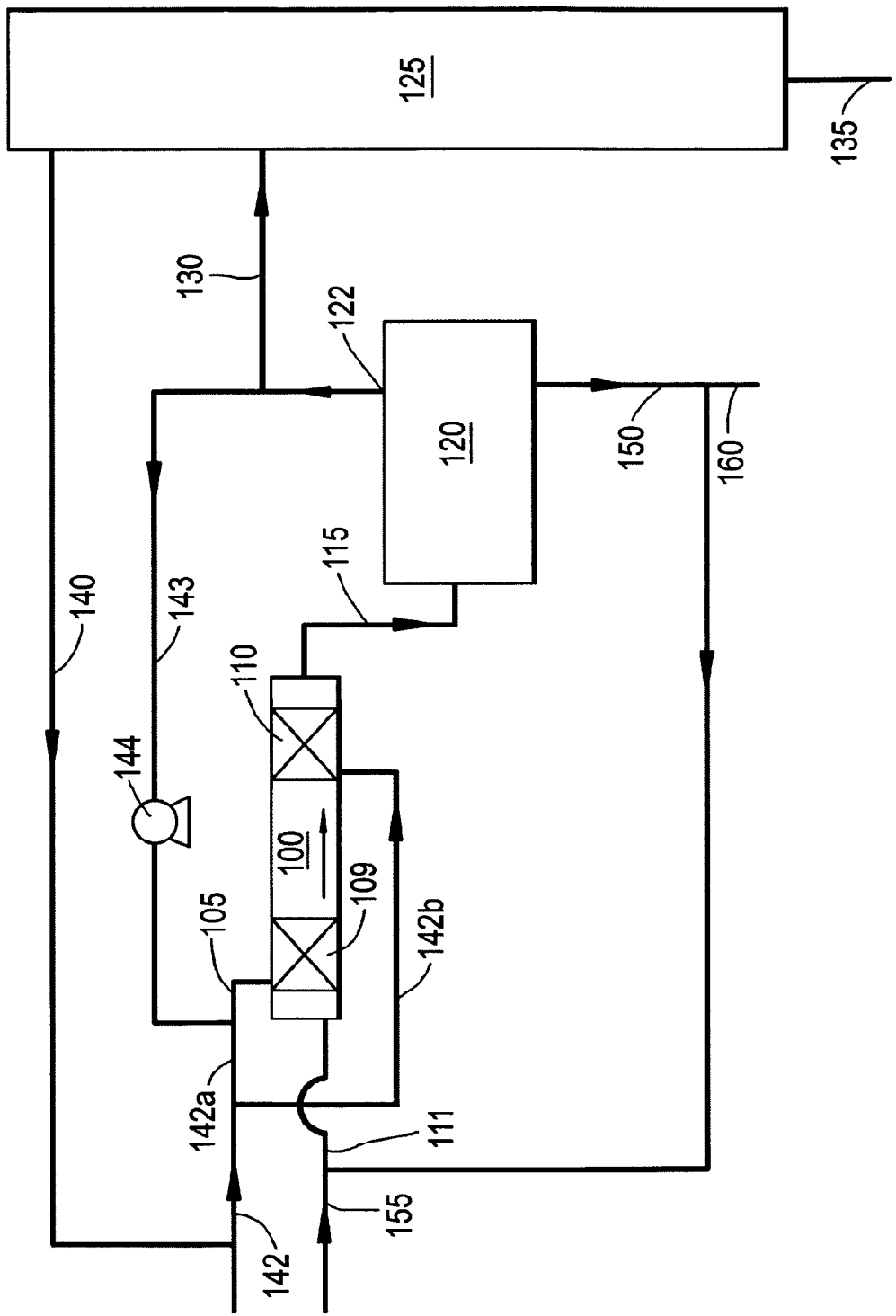
FIG. 1 provides a schematic overview of a process according to the invention.

In the process according to the invention an alkylate is prepared by reacting an isoparaffin with an olefin. The obtained alkylate is particularly suitable for gasoline blending purposes or for use in aviation gasoline production. In the process according to the invention the isoparaffin and the olefin are provided to a reaction zone. In the reaction zone a hydrocarbon mixture comprising isoparaffin and olefin is contacted with a catalyst suitable for alkylation.

In the present invention the catalyst is an acidic ionic liquid or a composite mixture comprising the ionic liquid (herein below also referred to a catalyst).

Ionic liquids are known in the art for their ability to catalyse alkylation reactions. The catalyst used in the present invention is a composite ionic liquid comprising cations derived from a hydrohalide of an alkyl-containing amine, imidazolium or pyridine. Preferably, the cations comprise nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of suitable cations include triethyl-ammonium ($NEt_3H^+$) and methyl-diethyl-ammonium cations ($MeNEt_2H^+$) or

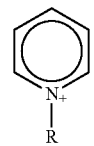

The anions of the composite ionic liquid are preferably aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulphate or nitrate to form a coordinate anion, in particular a coordinate anion derived from two or more metal halides, wherein at least one metal halide is an aluminium halide. Suitable further metal halides, sulphates or nitrates, may be selected from halides, sulphates or nitrates of metals selected from the group consisting of Group IB elements of the Periodic Table, Group IIB elements of the Periodic Table and transition elements of the Periodic Table. Examples of suitable metals include copper, iron, zinc, nickel, cobalt, molybdenum, or platinum. Preferably, the metal halides, sulphates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

As mentioned hereinabove, the hydrocarbon mixture comprising isoparaffin and olefin is contacted with the catalyst in the reaction zone. Due to the high activity of the acidic ionic liquid catalyst, it is preferred to provide a high isoparaffin to olefin ratio in the hydrocarbon mixture contacted with the acidic ionic liquid catalyst in the reaction zone. Preferably, the isoparaffin to olefin ratio in the hydrocarbon mixture is at least 20:1, more preferably at least 50:1, even more preferably at least 100:1. Preferably, the isoparaffin to olefin ratio is in the range of from 100:1 to 200:1. The hydrocarbon mixture is mixed in the reaction zone with the catalyst to form a reaction mixture. As the reaction progresses the reaction mixture will, besides hydrocarbon reactants and acidic ionic liquid, additionally comprise products. Mixing of the hydrocarbon mixture and the catalyst may be done by any suitable means for mixing two or more liquids, including dynamic and static mixers. In contact with the catalyst, the isoparaffins and olefins react under alkylation conditions to form an alkylate. The formed alkylate is obtained from the reaction zone by withdrawing an alkylate-comprising effluent from the reaction zone. It will be appreciated that due to the high isoparaffin to olefin ratio in the hydrocarbon mixture, the alkylate-comprising effluent still comprises a substantial amount of unreacted isoparaffin. At least part of, preferably all of, the alkylate-comprising effluent of the reaction zone is separated in a separator unit into a hydrocarbon-rich phase and an acidic ionic liquid catalyst-rich phase. Reference, herein to a hydrocarbon-rich phase is to a phase comprising more than 50 mol % of hydrocarbons, based on the total moles of hydrocarbon and acidic ionic liquid catalyst. Reference, herein to an acidic ionic liquid catalyst-rich phase is to a phase comprising more than 50 mol % of acidic ionic liquid catalyst, based on the total moles of hydrocarbon and acidic ionic liquid catalyst. Due to the low affinity of the acidic ionic liquid for hydrocarbons and the difference in density between the hydrocarbons and the acidic ionic liquid catalyst, the separation may be done using for example well known settler means, wherein the hydrocarbons and catalyst separate into an upper predominantly hydrocarbon phase and lower predominantly catalyst phase. However, settlers separate on the basis of gravity forces and may prove to provide insufficient separation capacity for separation the hydrocarbon and catalyst phases and require long residence times. This may result in:

carry over of catalyst to downstream hydrocarbon treating equipment;
contamination of alkylate-comprising hydrocarbon phase, resulting in off-spec products;
formation of hydrocarbon-catalyst emulsions in the settler, resulting in operational problems for settler level control;
decreased catalyst rejuvenation regeneration effectiveness, both in terms of capital cost (larger equipment) and effectiveness of catalyst activity recovery due to the inclusion of a larger fraction of alkylate-comprising hydrocarbon phase in the catalyst.

In addition, the hydrocarbon recycle volumes are high due to the high isoparaffin to olefin molar ratios used in an IL alkylation process as mentioned herein above. This requires the use of large volume settles, comprising undesirable large inventories of liquefied light hydrocarbons.

Therefore, it is preferred that the separation of at least part of the alkylate-comprising effluent into an hydrocarbon-rich phase and an ionic liquid catalyst-rich phase is performed by providing the alkylate-comprising effluent to a centrifugal separator and separating the alkylate-comprising effluent under the influence of centrifugal forces into an hydrocarbon-rich phase and an ionic liquid catalyst-rich phase.

The centrifugal separator may by any centrifugal separator suitable to separate at least two immiscible liquid phases. Preferably, the centrifugal separation unit is a cyclone type separation unit as such cyclone type separation units allow for a fast and continues separation of two immiscible liquid phases. Preferably, the cyclone is a hydro-cyclone. Reference herein to a hydro-cyclone is to a cyclone designed for the separation of water-hydrocarbon mixtures. Reference herein to a centrifugal separation unit is to a separation unit that can separate two liquid phases on the basis of centrifugal forces. Reference herein to a separation unit is a separation unit comprising one separator, e.g. a cyclone, or two or more separators, e.g. two cyclones, aligned in parallel.

By separating the alkylate-comprising effluent by providing it to a centrifugal separator it is possible separate the effluent continuously with short residence times in the separator. There is no need to provide large settler volumes filled with large amounts of liquefied light hydrocarbons to enable a high hydrocarbon recycle. This has significant safety benefits. Is also possible to use combinations of two or more cyclones and/or centrifugal separators, optionally combined with a settler. At least part of the catalyst phase, which is separated from the alkylate-comprising effluent is generally recycled back to the reaction zone.

As mentioned herein above, the alkylate-comprising effluent comprises significant amounts of unreacted isoparaffin. During the separation of the effluent in a hydrocarbon-rich phase and a catalyst phase, the isoparaffins accumulate in the hydrocarbon rich phase. Therefore, at least part of the hydrocarbon-rich phase is used to form the hydrocarbon mixture, which is provided to the reaction zone, by mixing the part of the hydrocarbon-rich phase, i.e. without further fractionation, with an olefin-comprising stream. The obtained hydrocarbon mixture thus comprises olefin predominantly supplied externally, i.e. fresh olefin, and comprises isoparaffin. The isoparaffin may be externally supplied isoparaffin, i.e. fresh isoparaffin, but also isoparaffin obtained from the fractionator unit as described herein below, however part of the isoparaffin is provided by recycling the hydrocarbon-rich phase from the separator. The fresh isoparaffin and olefin may be supplied to the process separately, however typically the fresh isoparaffin and the fresh olefin are provided to the reaction zone as a stream comprising isoparaffin and olefin, for instance by adding isoparaffin to the olefin-comprising stream. By using part of the hydrocarbon-rich phase to form the hydrocarbon mixture, a high isoparaffin to olefin ratio in the hydrocarbon mixture is obtained in the hydrocarbon mixture.

It would be possible to provide the olefin-comprising stream directly into the reaction zone without prior mixing with the hydrocarbon-rich phase or by mixing the olefin-comprising stream with part of the alkylate-comprising effluent, which in addition to hydrocarbons still contains significant amounts of catalyst. However, by doing so a relatively concentrated olefin stream is brought in direct contact with the catalyst and as a consequence side reaction may occur such as olefin polymerisation, which result in a decrease alkylate yield.

In the process according to the invention the olefin-comprising stream is first mixed with the hydrocarbon-rich phase prior to contacting the catalyst. This is beneficial as the hydrocarbon-rich phase contains little catalyst, which prevents any undesired side reactions such as olefin polymerisations. By mixing the olefin-comprising stream with the hydrocarbon-rich phase the isoparaffin to olefin is set to the desired high ratio before significant catalytic reactions can commence.

At least part of the hydrocarbon-rich phase is treated and/or fractionated to retrieve an alkylate-comprising product. During fractionation an alkylate-comprising stream, an isoparaffin-comprising stream and optionally a stream comprising other hydrocarbons such as n-butanes may be obtained.

The hydrocarbon mixture obtained by mixing the olefin-comprising steam and part of the hydrocarbon-rich phase is provided to the reaction zone and contacted with the acid ionic liquid catalyst to form the alkylate.

Preferably, reaction zone comprises two or more sections allowing for inter-stage feeding. Preferably, the hydrocarbon mixture is supplied to the first section while separate olefin-comprising streams are fed by inter-stage feeding to each subsequent section. This has the advantage that less hydrocarbon phase needs to be recycled as only part of the total olefin feed is mixed with the hydrocarbon phase recycle. Less olefin means that less isoparaffin is needed to maintain a high isoparaffin to olefin molar ratio in the hydrocarbon mixture, while the high isoparaffin containing product mixture from the previous reaction section is used to generate a high isoparaffin to olefin ratio in the next reaction section, As a result the size of the total reaction and separation unit may be reduced.

The separate olefin-comprising streams may obtained by splitting the olefin-comprising stream prior to mixing with the hydrocarbon-rich phase.

Alternatively, at least part of the hydrocarbon mixture is provided to each section by inter-staged feeding of hydrocarbon mixture. This has the advantage that sufficient olefin may be provided to the reaction zone without the need to introduce a hydrocarbon mixture having a lower isoparaffin to olefin ratio at the inlet of the reaction zone.

In case of inter-staged feeding of the hydrocarbon mixture into separate section of the reaction zone, it is preferred that the distance in term of residence time between two separate hydrocarbon feed points or inlets is larger than the residence time required to convert at least 90 mol % of the olefin provided to the reaction zone in the previous section. This ensures that the isoparaffin to olefin ratio in the reaction zone remains high.

Preferably the hydrocarbon mixture is continuously mixed with the acidic ionic liquid catalyst in the reaction zone. Preferably, mixing is achieved by providing one or more static mixers in the reaction zone. Preferably such a static mixer is located directly following or even overlapping the inlet for introducing the hydrocarbon mixture in the reaction zone or section thereof.

It has been observed that during the alkylation reaction solids are formed in the reaction zone. Reference, herein to solids is to non-dissolved solid particles. The solids predominantly consist out of metals, metal compounds and/or metal salts which were originally comprised in the acidic liquid catalyst. Preferably, the solids comprise at least 10 wt % metal, i.e. either in metallic, covalently bound or ionic form, based the total weight of the solids, wherein the metal is a metal that was introduced to the process as part of the acidic ionic liquid catalyst. The solids may also comprise components, which were introduced into the reaction mixture as contaminants in the hydrocarbon mixture or the acidic ionic liquid. Alternatively, the solids may be the product of a chemical reaction involving any of the above-mentioned compounds.

The solids may have any size, however it was found that the solids typically have an average size of in the range of from 0.1 to 10 µm. In particular, at least 50% of the solids have a particle size below 5 µm, more particular 80% of the solids have a particle size below 5 µm based on the total number of solid particles.

Although, during mixing these solids are dispersed throughout the reaction mixture, upon separation of the alkylate-comprising effluent it has been found that the solids, i.e. to a large extent, accumulate in the acidic ionic liquid catalyst-rich phase. This is due to the high density of the solids. The catalyst-rich phase is subsequently recycled to the reaction zone to become part of the reaction mixture in the reaction zone. As a result, the solids accumulate in the reaction zone, resulting in undesirable solids content in the reaction zone. A high solids content in the reaction zone may for instance result in blockage of pathways or valves in the reaction zone and pipes to and from the separation unit, due to precipitation of solids. In addition, at high solids content the solids may agglomerate to form large aggregates, resulting in increased blockage risk.

In the present invention, at least part of the solids are removed from the reaction zone. Preferably, solids are removed from the reaction zone to an extent that the reaction mixture, i.e. a mixture comprising hydrocarbon reactants, acidic ionic liquid and products, comprises at most 5 wt % of solids, preferably at most 2 wt % of solids, based on the total weight of the acidic ionic liquid in the reaction zone. It is not required to remove all solids from the reaction zone, preferably, solids are removed from the reaction zone to an extent that the reaction zone comprises in the range of from 0.05 to 5 wt %, more preferably of from 0.1 to 2 wt % of solids, based on the total weight of the acidic ionic liquid in the reaction zone.

The solids may be removed from the reaction zone at any time or place in the process. It is possible to remove the solids from the reaction mixture directly inside the reaction zone. However, preferably, the solids are removed from a stream, which has been withdrawn from the reaction zone. It has been found that the solids accumulate in the catalyst-rich phase formed in the separator unit. Therefore, it is preferred to remove the solids from the catalyst-rich phase prior to reintroducing the catalyst into the reaction zone.

The solids may be removed by any suitable means for removing solids from liquids, including but not limited to filtration, precipitation and centrifugation processes. Such processes are well known in the art.

Due to the specific nature of ionic liquids it is preferred that the removal of the solids is performed at such a temperature that the acidic ionic liquid catalyst is liquid. In particular, it is preferred to remove the solids at a temperature in the range of from 5 to 80° C., more preferably of from 20 to 60° C., while ensuring that the temperature is such that the ionic liquid remains a liquid. By removing the solids at elevated temperatures, the viscosity of the ionic liquid is lower while the density is reduced, which may be beneficial in view of decreased time and power input required to obtained separation of the solids from the liquid.

The solids may be removed from the process in any form, typically the solids will be removed in the form of a slurry of solids. Such a slurry may comprise next to the solids for instance some residual acidic ionic liquid. The slurry may be further treated to extract the residual acidic ionic liquid. This is preferably done using a liquid-liquid extraction process with a suitable solvent. Due to the virtual absence of an ionic liquid vapour pressure, the solvent can be easily recovered by for instance evaporation and subsequent condensation. The recovered solvent can be reused.

Although, it is believed that part of the catalyst is lost when forming the solids, the catalyst alkylation performance is not significantly affected. Loss of catalyst due to solids formation merely means that a small fraction of the total catalyst inventory is inactivated or lost, while the remainder of the catalyst remains unaffected.

Optionally, catalyst can be contacted with an acid, preferably a hydrogen halide, more preferably hydrogen chloride, to rejuvenate the catalyst. This can be done by introducing, i.e. adding, hydrogen chloride into the process. Preferably, the acidic ionic liquid catalyst is rejuvenated prior to recycling the catalyst-rich phase to the reaction zone. The acidic ionic liquid catalyst in the catalyst-rich phase, which is recycled is rejuvenated by addition of hydrogen chloride to at least part of the recycled catalyst-rich phase.

By rejuvenation the acidic ionic liquid catalyst after separation of the alkylate-comprising effluent into a catalyst-rich phase and a hydrocarbon-rich phase, undesired chlorination of hydrocarbons is reduced. The hydrogen chloride reacts with the acidic ionic liquid catalyst. Hydrogen chloride is added until no hydrogen chloride is consumed any longer, i.e. until saturation. Hydrogen chloride consumption can be followed by measuring the pressure. Preferably, the addition of hydrogen chloride is done in regular steps, while measuring the pressure in between each addition step. By adding the hydrogen chloride in small steps the creation of an undesired hydrogen chloride gas cap upon saturation is reduced.

The addition of hydrogen chloride may be done by injecting the hydrogen chloride into one or more units or into one or more streams passing from one unit to the next. Hydrogen chloride addition may for instance be done using a venture absorber, preferably a venture absorber located downstream from the means for removing solids.

As mentioned herein above, although some gaseous hydrogen chloride in the reaction zone may be tolerated, it is undesired to accumulate unreacted gaseous hydrogen chloride in the reaction system as a result of over-saturation of the acidic ionic liquid with hydrogen chloride. Residual gaseous hydrogen chloride may be purged from the reaction system by for instance flushing with an inert gas such as nitrogen. However, such process would require additional means for providing nitrogen gas and subsequent storage and treatment of hydrogen chloride-contaminated nitrogen gas. In addition, part of the hydrogen chloride is provided for rejuvenation is lost. Preferably, such hydrogen chloride accumulation is reduced by mixing additional spent acidic ionic liquid catalyst, e.g. in the form of a spent catalyst-comprising stream, into the rejuvenated acidic ionic liquid catalyst comprising catalyst-rich phase, i.e. the recycled catalyst-rich phase comprising added hydrogen chloride. Reference, herein to spent acidic ionic liquid catalyst is to an acidic ionic liquid catalyst, which has been used as a catalyst in a chemical reaction and has not yet been rejuvenated with hydrogen chloride. By allowing the spent acidic ionic liquid to react with the gaseous hydrogen chloride present due to initial over-saturation, the remaining hydrogen chloride may be consumed. The spent ionic liquid catalyst may be introduced from an external source, however it is also possible to allow part of the ionic liquid catalyst-rich phase or to bypass the rejuvenation and subsequently mix the rejuvenated and bypassed streams.

The solids, which are removed from the process may be discarded, however it is preferred to reuse the components in the solids, for example in the preparation of fresh acidic ionic liquid catalyst.

In the process according to the invention, an isoparaffin and an olefin are reacted to form an alkylate by contacting the hydrocarbon mixture comprising isoparaffin and olefin with the catalyst under alkylation conditions.

Preferably, the hydrocarbon mixture comprises at least isobutane, isopentane or a mixture thereof as an isoparaffin. The hydrocarbon mixture preferably comprises at least an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

Isoparaffins and olefins are supplied to the process in a molar ratio, which is preferably 1 or higher, and typically in the range of from 1:1 to 40:1, more preferably 1:1 to 20:1. In the case of continuous reaction, excess isoparaffin can be recycled for reuse in the hydrocarbon mixture.

The alkylation conditions (or process conditions) are those known in the art for HF and sulphuric acid alkylation. Actual operational process conditions are among others dependent of the exact composition of the hydrocarbon mixture and catalyst.

The temperature in the reaction zone is preferably in the range of from −20 to 100° C., more preferably in the range of from 0 to 50° C. In any case the temperature must be high enough to ensure that the ionic liquid catalyst is in the liquid state.

To suppress vapour formation in the reaction zone, the process is performed under pressure, preferably the pressure in the reaction zone is in the range of from 0.1 to 1.6 MPa.

The hydrocarbon mixture may be contacted with the catalyst in any suitable alkylation reactor. The hydrocarbon mixture may be contacted with the catalyst in a semi-continues or continuous process.

Preferably, the acidic ionic liquid catalyst to hydrocarbon volumetric ratio in the reaction zone is at least 0.5, preferably 0.9 more preferably at least 1. Preferably, the acidic ionic liquid catalyst to hydrocarbon ratio in the reaction zone is in the range of from 1 to 10.

The hydrocarbon-rich phase obtained after phase separating the alkylate-comprising effluent in a hydrocarbon-rich phase and a catalyst-rich phase, may be treated to fractionate the hydrocarbon-rich phase and to retrieve the alkylate and optionally other components in the hydrocarbon phase, such as unreacted isoparaffin or n-paraffins.

The hydrocarbon-rich phase may be treated by any suitable way to fractionate a hydrocarbon stream, such a distillation.

Following the fractionation, the obtained alkylate or alkylate comprising product may be used to prepare avgas or as a blending component for gasoline. As mentioned, the hydrocarbon-rich phase may also comprise isoparaffin. Preferably, such isoparaffin is at least partly reused to form part of the isoparaffin feed provided to the process. This may be done by recycling at least part of the isoparaffin, or a stream comprising isoparaffin obtained from the fractionation of the hydrocarbon-rich phase, and combining it with the isoparaffin and/or olefin-comprising stream, which will be used to form the hydrocarbon mixture.

In FIG. 1, a process according to the invention is schematically represented. In FIG. 1, hydrocarbon mixture 105, comprising olefin and isoparaffin is provided to reaction zone 100. Hydrocarbon mixture 105 is provided to first reaction zone section 109, comprising a static mixing device. Acidic ionic liquid catalyst 111 is also provided reaction zone 100. In reaction zone 100, the hydrocarbon mixture and catalyst are contacted under alkylation conditions. Alkylate-comprising effluent 115 is withdrawn from reaction zone 100 and supplied to settler unit 120. In settler unit 120, a hydrocarbon-rich phase and a catalyst-rich phase separate under influence of gravity. Hydrocarbon-rich phase 122 is withdrawn from separator unit 120. A part of hydrocarbon-rich phase 122 is provided to fractionator unit 125 via conduit 130. From the bottom of fractionator unit 125, an alkylate-comprising product is retrieved through conduit 135. The alkylate product can for instance be used for fuel blending purposes.

Additionally, isoparaffin-comprising stream 140 is retrieved from fractionator unit 125, which is recycled to become part of the olefin-comprising stream 142, which is then split into olefin comprising stream 142a and 142b. Other hydrocarbon-comprising streams (not shown) may also be retrieved from fractionator 125.

Another part of the hydrocarbon-rich phase 122 is combined with olefin-comprising stream 142a via conduit 143 to form hydrocarbon mixture 105. Olefin comprising stream 142b is provided to second reaction zone section 110, comprising a static mixing device and located downstream of first reaction zone section 109.

Circulation pump 144 has been provided in conduit 143 to assist the recycling of hydrocarbon-rich phase 122.

Ionic liquid catalyst-phase 150 is withdrawn from separator unit 120 and provided back to reaction zone 100 and combined with acidic ionic liquid catalyst 111, which may also comprise fresh catalyst 155. If necessary spent acidic ionic liquid may be withdrawn from the process via conduit 160.

Figure 2:
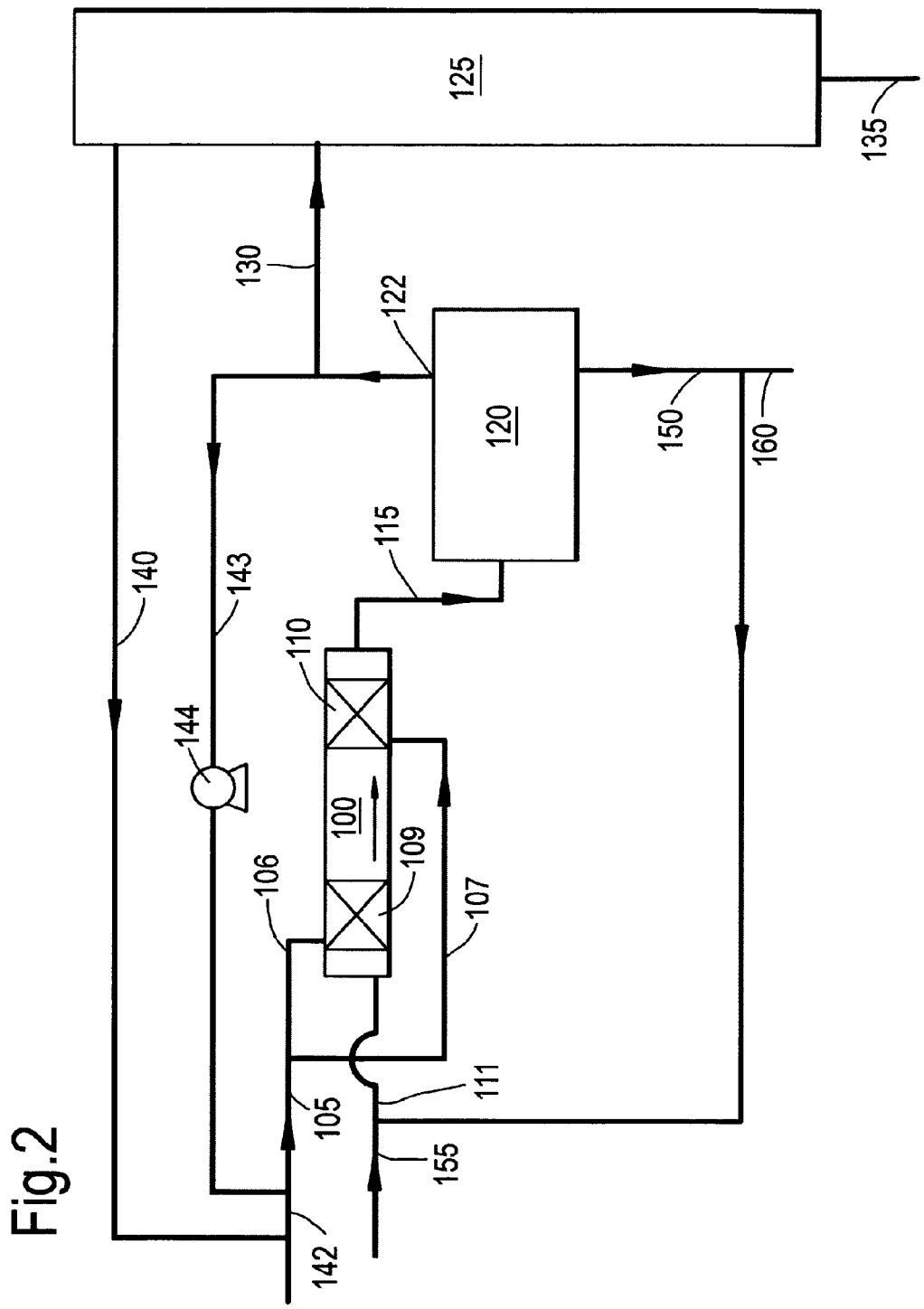
FIG. 2 is a schematic overview of another process according to the invention. version.

In FIG. 2, another process according to the invention is schematically represented. In FIG. 2, hydrocarbon mixture 105, comprising olefin and isoparaffin is first split into a first hydrocarbon mixture 106 and second hydrocarbon mixture 107, which are separately provided to first reaction zone section 109 and second reaction zone section 110 located downstream of first reaction zone section 109, each section comprising a static mixing device.

Hydrocarbon-rich phase 122 is combined with olefin-comprising stream 142 via conduit 143 to form hydrocarbon mixture 105.

What is claimed is:

1. A process for preparing an alkylate, comprising:
    contacting in a reaction zone a hydrocarbon mixture comprising at least isoparaffin and an olefin with an acidic ionic liquid catalyst under alkylation conditions to obtain an alkylate;
    withdrawing an alkylate-comprising effluent from the reaction zone;
    separating at least part of the alkylate-comprising effluent into an hydrocarbon-rich phase and an ionic liquid catalyst-rich phase, wherein the separated hydrocarbon-rich phase comprises alkylate and isoparaffin;
    fractionating part of the hydrocarbon-rich phase into at least an alkylate-comprising product and a isoparaffin-comprising stream;
    mixing another part of the hydrocarbon-rich phase, without further fractionation, with an olefin-comprising stream to form the hydrocarbon mixture; and
    providing the hydrocarbon mixture to the reaction zone.

2. A process according to claim 1, wherein the step of separating at least part of the alkylate-comprising effluent into an hydrocarbon-rich phase and an ionic liquid catalyst-rich phase, comprises providing the at least part of the alkylate-comprising effluent to a centrifugal separator and separating the alkylate-comprising effluent under influence of centrifugal forces.

3. A process according to claim 2, wherein the reaction zone comprises two or more sections and the hydrocarbon mixture is provided to a first section, wherein a separate olefin-comprising stream is provided to subsequent reaction zones by inter-staged feeding of separate olefin-comprising streams.

4. A process according to claim 1, wherein the reaction zone comprises two or more sections and at least part of the hydrocarbon mixture is provided to each section by inter-staged feeding of hydrocarbon mixture.

5. A process according to claim 4, wherein at least part of the acid ionic liquid catalyst-rich phase is recycled to the reaction zone.

6. A process according to claim 5, wherein the hydrocarbon mixture comprises isoparaffins and olefins in an isoparaffin to olefins molar ratio of at least 20:1.

7. A process according to claim 6, wherein isoparaffin is provided to process separately as part of the olefin-comprising stream.

8. A process according to claim 7, wherein isoparaffin and olefin are provided to the process in an isoparaffin to olefin molar ratio in the range of from 1:1 to 40:1.

9. A process according to claim 7, wherein the isoparaffin is isobutane and/or isopentane.

10. A process according to claim 9, wherein the olefin-comprising stream comprises an olefin comprising in the range of from 3 to 6 carbon atoms.

11. A process according to claim 10, wherein the acidic ionic liquid catalyst is a composite ionic liquid comprising of cations derived from a hydrohalide of an alkyl-containing amine or pyridine, anions being composite coordinate anions derived from two or more metal halides, wherein at least one metal halide is an aluminium halide and any further metal halide is a halide of a metal selected from the group consisting of Group IB elements of the Periodic Table, Group IIB elements of the Periodic Table and transition elements of the Periodic Table.

12. A process according to claim 11, wherein to the catalyst comprises aluminium chloride and copper (I) chloride or copper (II) chloride.

13. A process according to claim 5, wherein the hydrocarbon mixture comprises isoparaffins and olefins in an isoparaffin to olefins molar ratio of at least 50:1.

14. A process according to claim 9, wherein the olefin-comprising stream comprises an olefin comprising in the range of from 4 to 5 carbon atoms.

15. A process according to claim 14, wherein the hydrocarbon mixture comprises isoparaffins and olefins in an isoparaffin to olefins molar ratio in the range from 100:1 to 200:1.

* * * * *